United States Patent [19]

Caprioli et al.

[11] Patent Number: 4,503,042

[45] Date of Patent: Mar. 5, 1985

[54] ACARICIDE COMPOSITIONS

[75] Inventors: Vincenzo Caprioli, S. Martino; Angelo Longoni; Pietro Massardo, both of Milan, all of Italy

[73] Assignee: Montedison S.p.A., Milan, Italy

[21] Appl. No.: 413,830

[22] Filed: Sep. 1, 1982

[30] Foreign Application Priority Data

Sep. 2, 1981 [IT] Italy ................................ 23726 A/81

[51] Int. Cl.$^3$ ...................... A01N 59/20; A01N 55/02
[52] U.S. Cl. ..................................... 424/141; 514/499
[58] Field of Search ................................ 424/141, 294

[56] References Cited

U.S. PATENT DOCUMENTS 2,891,984 6/1959 Gatzi et al. .......................... 424/141
3,773,926 11/1973 Knowles et al. ..................... 424/141
4,388,323 6/1983 Massardo et al. ................... 424/311

FOREIGN PATENT DOCUMENTS 2100380 3/1980 Italy .
2620580 11/1980 Italy .
2640180 12/1980 Italy .
50-69224 6/1975 Japan ................................... 424/141
37092 7/1981 United Kingdom .

OTHER PUBLICATIONS

Chemical Abstracts 90:49599z (1978).

Primary Examiner—Albert T. Meyers
Assistant Examiner—John M. Kilcoyne

[57] ABSTRACT

Acaricide mixtures obtained from the synergistic coupling of an acaricide belonging to the class of the hydroquinone diethers with metallic copper or copper compounds and the use of said mixtures in suitable compositions in the treatment of mite infestations on useful plants are disclosed.

9 Claims, No Drawings

ACARICIDE COMPOSITIONS

BACKGROUND OF THE INVENTION

Italian patent applications No. 21003 A/80, No. 26205 A/80 and No. 26401 A/80, which are the priority documents for Massaro et al U.S. Pat. No. 4,388,323, issued June 14, 1983, describe, among other compounds, the compounds of formula I and the use thereof as acaricides:

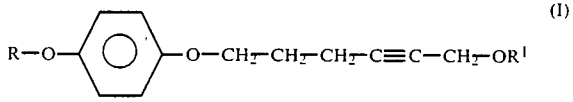

wherein R is an alkyl $C_8$-$C_{11}$, $R^1$ is a hydrogen atom, an alkyl $C_1$-$C_4$, an alkenyl $C_2$-$C_4$ or a group

in which $R^2$ is an alkyl $C_1$-$C_4$, a cycloalkyl $C_3$-$C_6$ or phenyl.

The compounds of formula I are endowed with a high acaricide activity which is exerted mainly against mite eggs.

It is known that a few copper compounds, such as copper sulphate, copper hydroxide, copper oxychloride, copper (I) chloride, copper protoxide and copper carbonate possess fungicidal properties and are widely employed also in admixture with one another for protecting plants from infections due to fungi.

It is furthermore disclosed in the literature that some copper salts, including copper oxychloride, exert a repellent action on *Leptinotarsa decemlineata* larvae and that they are employable, in admixture with insecticides, in the fight against such coleopter [Khim. Sel'sk. Khoz. 16 (11), 65 (1978); Chem. Abstr. 90:49599z].

As far as we know, however, a possible acaricide activity of copper compounds or of metallic copper has never been reported in the literature.

Moreover, tests carried out by use have confirmed that metallic copper and copper compounds do not possess any acaricide activity in particular against mite eggs.

Instead, we have surprisingly found that the coupling of copper compounds or of metallic copper with an acaricide compound of formula I synergizes the acaricide activity of the latter.

Thus, one object of the present invention is to provide synergistic mixtures endowed with acaricide activity, and consisting of a compound of formula I and of a copper compound or of metallic copper in a ratio by weight of from 1:1 to 1:250, referred to the metallic copper or to the copper content of the copper compound.

Metallic copper can be employed in the aforementioned mixtures in a finely divided form like that of electrolytic copper.

The copper compounds employable in the synergistic mixtures of this invention may be oxides, hydroxide, organic and inorganic salts of mono or divalent copper, also in admixture with one another. Useful compounds include:
copper (II) sulphate $CuSO_4$
copper (I) chloride $CuCl$
copper (II) chloride $CuCl_2$
copper (II) carbonate $CuCO_3$
copper protoxide $Cu_2O$
copper (II) hydroxide $Cu(OH)_2$
copper oxychloride (a mixture of copper hydroxide and chloride)
and mixtures thereof.

Since the acaricide action of the compunds of formula I is synergized when they are employed in the form of the mixtures of this invention, it follows that such mixtures offer also the considerable advantage of allowing reduction of the doses of compounds of formula I required while providing the same acaricide effectiveness.

The mixtures according to the present invention can be utilized in agriculture for protecting the plants against infestations due to acari.

The main acari of particular economic interest owing to the damages caused to the plants and owing to their very extensive diffusion in all cultivated areas belong prevailingly to family Tetranychidae, genera Tetranychus (*T. urticae, T. telarius, T. pacificus*, etc.), Panonychus (*P. ulmi, P.citri*, etc.), Bryobia (*B. praetiosa*) and Oligonychus.

Further species noxious to the cultures belong, for example, to family Eriophydae (genera Aceria, Eriophyes, Phyllocoptes, Phyllocoptruta, Vasates, etc.), Tarsonemidae genus Hemitarsonemus and Tenuipalpidae.

For practical use in agriculture, the mixtures of the present invention may be employed as such or in the form of agriculturally acceptable compositions or formulations.

Said compositions can contain, in addition to the synergistic mixture as active substance, solid or liquid inert vehicles as well as, optionally, other compatible additives, such as surfactants, suspending agents, emulsifiers, dispersants, adhesion promoting agents and the like.

According to the usual formulating practice, the compositions may be in the form of dry powders, wettable powders, pastes, concentrated emulsions, emulsifiable liquids, etc.

The synergistic mixture may be contained in said compositions in amounts ranging from 0.5 to 95% by weight depending on the type of composition and on the particular use for which it is intended.

The amount of acaricide mixture to be distributed in the area or on the vegetation to be protected depends on various factors such as the type of composition employed, the available application means, the degree and nature of the infestation, the type of culture to be protected, and the climatic and environmental conditions.

Generally, amounts of the synergistic acaricide mixture ranging from 0.1 to 2 kg/ha are sufficient for a very effective protection of the cultures from mite infestations.

If desirable, it is possible to prepare an extemporary mixture just prior to treatment.

Since many of the copper compounds employed are also endowed with a fungicide activity, it is logically expectable that mixtures of the invention exhibit also a fungicide activity.

The above-described formulations may be optionally additioned with other compatible active substances selected from among insecticides, acaricides, fungicides, phyto growth regulators, fertilizers, etc.

The compounds of formula I are furthermore endowed with an acaricide activity against hibernating eggs of acari. For this use, they can be employed as such or in compositions which contain, optionally, mineral oils. It is possible to employ the mixtures according to the present invention also for treatments against hibernating eggs of acari, optionally in compositions containing also such mineral oils.

The following examples are given to illustrate the invention in more detail and are not intended to be limiting.

EXAMPLE 1

Demonstration of the synergistic effect

The acaricide activity of individual compounds and of mixtures according to the present invention was evaluated on *Tetranychus urticae* eggs, such acarus being particularly representative due to the damages it causes to plants and to its wide diffusion.

The acaricide activity was determined according to the following general methodology:

Small discs cut from bean leaves were infested with adult females of the acarus, successively removed after the egg deposition.

The egg-carrying discs were then sprayed with a hydroacetonic dispersion of the product or mixture being tested, at a predetermined concentration.

For comparative purposes, other discs were sprayed only with hydroacetonic solution.

Seven days after the treatment, the percentage of unhatched eggs (equivalent to the percentage of mortality) was ascertained in comparison with that of the check.

Until conclusion of the data collecting, the discs were kept at 25° C., 70% of relative humidity and under continuous light.

As compounds of formula I, the compounds of formula

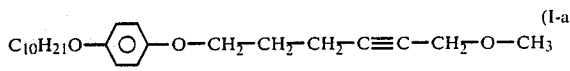

(I-a)

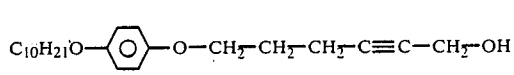

(I-b)

were employed.

As copper compounds, the following were utilized:
copper (II) sulphate $CuSO_4$
copper protoxide $Cu_2O$
copper oxychloride (technical grade)
copper (I) chloride $CuCl$
copper (II) chloride $CuCl_2$
copper (II) carbonate $CuCO_3$ and
electrolytic metallic copper.

The acaricide activity on eggs of *Tetranychus urticae* exerted by the above-listed compounds separately employed is recorded in the following Table 1, where it is expressed as percentage of unhatched mite eggs at the indicated doses.

TABLE 1

| Compound | Dose (ppm of a.i.) | Percentage of unhatched mite eggs | Approximate copper content |
|---|---|---|---|
| I-a | 0.5 | 64 | — |
| I-b | 0.5 | 44 | — |
| $CuSO_4$ | 1000 | 0 | 40% |
|  | 125 | 0 |  |
|  | 25 | 0 |  |
| $Cu_2O$ | 1000 | 0 | 89% |
|  | 125 | 0 |  |
|  | 25 | 0 |  |
| Copper oxychloride (technical grade) | 1000 | 0 | 51% |
|  | 125 | 0 |  |
|  | 25 | 0 |  |
| $CuCl$ | 1000 | 0 | 64% |
|  | 125 | 0 |  |
|  | 25 | 0 |  |
| $CuCl_2$ | 1000 | 0 | 47% |
|  | 125 | 0 |  |
|  | 25 | 0 |  |
| $CuCO_3$ | 1000 | 0 | 51% |
|  | 125 | 0 |  |
|  | 25 | 0 |  |
| Electrolytic copper | 1000 | 0 | 100% |
|  | 125 | 0 |  |
|  | 25 | 0 |  |

The acaricide activity of mixtures according to this invention is recorded in the following Table 2.

TABLE 2

| Mixture components | Doses (ppm of a.s.) | Approx. ratio 1/Cu b.w. | Percentage of unhatched eggs Found | Percentage of unhatched eggs Expected |
|---|---|---|---|---|
| I-a $CuSO_4$ | 0.5 125 | 1:100 | 87 | 64 |
| I-a $CuSO_4$ | 0.5 25 | 1:20 | 88 | 64 |
| I-a $Cu_2O$ | 0.5 125 | 1:220 | 88 | 64 |
| I-a $Cu_2O$ | 0.5 25 | 1:44 | 69 | 64 |
| I-a Oxychloride | 0.5 125 | 1:127 | 98 | 64 |
| I-a Oxychloride | 0.5 25 | 1:25 | 96 | 64 |
| I-a CuCl | 0.5 125 | 1:160 | 83 | 64 |
| I-b CuCl | 0.5 125 | 1:160 | 90 | 44 |
| I-a $CuCl_2$ | 0.5 125 | 1:117 | 92 | 64 |
| I-a $CuCl_2$ | 0.5 25 | 1:23 | 81 | 64 |
| I-b $CuCl_2$ | 0.5 125 | 1:117 | 80 | 44 |
| I-b $CuCl_2$ | 0.5 25 | 1.23 | 89 | 44 |
| I-b $CuCO_3$ | 0.5 125 | 1:127 | 60 | 44 |
| I-a Electrolytic Cu | 0.5 125 | 1:250 | 75 | 64 |
| I-b Electrolytic Cu | 0.5 125 | 1:250 | 56 | 44 |

Since the acaricide activity of metal copper and of the copper compounds reported in Table 1 proved to be null even at higher doses than those in the mixtures recorded in Table 2, it could have been expected that the acaricide activity of the mixtures of Table 2 might be at the most equal to the one of compounds I-a and I-b taken individually.

Conversely, the data reported in Table 2 unequivocally prove that the acaricide action of compounds I-a and I-b is synergized if such compounds are used in mixtures with metal copper or copper compounds.

EXAMPLE 2

Acaricide activity in the open field against acari of species *Panonychus ulmi*

Apple-trees, cultivated in the open field, naturally and uniformly infested by a mixed population of *Panonychus ulmi*, were treated by spraying up to dripping, by means of a motor pump, with aqueous dispersions of the product and of the mixture being tested. An equal number of plants having the same degree of infestation were used as check.

At successive intervals of time after the treatment, the degree of infestation of the treated plants in comparison with the check was determined by taking, from each tree, samples of leaves on which the population present was counted.

The acaricide activity was expressed as percentage of infestation reduction in respect of the check, and the results are recorded in the following Table 3.

TABLE 3

| Product or mixture | Dose (g of a.s./hl) | Approx. ratio I-a/Cu b.w. | Percent activity at the following intervals after treatment | |
|---|---|---|---|---|
| | | | 6 days | 14 days |
| I-a | 20 | — | 81 | 92 |
| Technical oxychloride | 50 | — | 0 | 0 |
| I-a oxychloride | 20 50 | 1:1.25 | 89 | 98 |

What is claimed is:

1. An acaricide mixture consisting of (a) at least one compound of formula

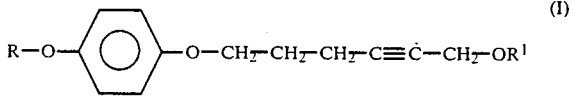

wherein
R is an alkyl $C_8$–$C_{11}$ and
$R^1$ is a hydrogen atom or an alkyl $C_1$–$C_4$; and
(b) finely divided metallic copper or a copper compound selected from the group consisting of the oxide, hydroxide, organic and inorganic salts of mono- and divalent copper, and mixtures thereof, in a ratio ranging from 1:1 to 1:250 by weight, referred to the metallic copper or to the copper content of the copper compound.

2. A mixture according to claim 1, in which the compound of formula I is the compound of formula

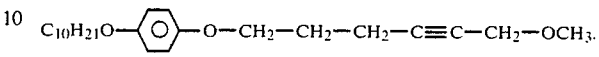

3. A mixture according to claim 1, in which the compound of formula I is the compound of formula

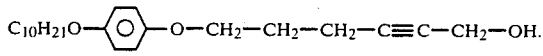

4. A mixture according to claim 1, in which the copper compound is selected from the group consisting of
copper (II) sulphate $CuSO_4$
copper protoxide $Cu_2O$
copper (I) chloride CuCL
copper (II) chloride $CuCl_2$
copper (II) carbonate $CuCO_3$
copper oxychloride which is a mixture of copper hydroxide and copper chloride, and mixtures thereof.

5. A mixture according to claim 1, in which the metallic copper is electrolytic copper.

6. The method of treating mite infestations on useful plants consisting in distributing on the plants an effective amount of a mixture according to claim 1, either as such or in the form of an agriculturally acceptable composition.

7. An acaricide composition containing a mixture according to claim 1 as active ingredient, inert vehicles and, optionally, other additives compatible with the acaricide mixture.

8. A method of treating mite infestations on useful plants consisting in distributing on the plants an effective amount of a mixture according to claim 2.

9. A method of treating mite infestations on useful plants consisting in distributing on the plants an effective amount of a mixture according to claim 3.

* * * * *